United States Patent [19]

Hinsken et al.

[11] 4,408,051
[45] Oct. 4, 1983

[54] 1-OXA-3,8-DIAZASPIRO[4.5]DECANES

[75] Inventors: Hans Hinsken, Kandern, Fed. Rep. of Germany; Wolfgang Mueller, Allschwil, Switzerland; Hermann Schneider, Granzach-Wyhlen, Fed. Rep. of Germany

[73] Assignee: Sandoz Ltd., Basel, Switzerland

[21] Appl. No.: 331,986

[22] Filed: Dec. 18, 1981

[30] Foreign Application Priority Data

Dec. 24, 1980 [DE] Fed. Rep. of Germany ....... 3049041

[51] Int. Cl.$^3$ ............................................. C07D 405/04
[52] U.S. Cl. .......................................... 546/19; 524/99
[58] Field of Search .......................................... 346/19

[56] References Cited

U.S. PATENT DOCUMENTS

| | | | |
|---|---|---|---|
| 4,107,139 | 8/1978 | Mayer et al. | 546/19 |
| 4,110,334 | 8/1978 | Mayer et al. | 546/19 |
| 4,247,449 | 1/1981 | Wiezer et al. | 546/19 |
| 4,263,505 | 4/1981 | Slongo et al. | 546/19 |
| 4,319,030 | 3/1982 | Wiezer et al. | 546/19 |

*Primary Examiner*—Robert T. Bond
*Attorney, Agent, or Firm*—Gerald D. Sharkin; Richard E. Vila; Frederick H. Weinfeldt

[57] ABSTRACT

Compounds obtained by the addition of unsaturated esters to the >NH group of compounds of formula II

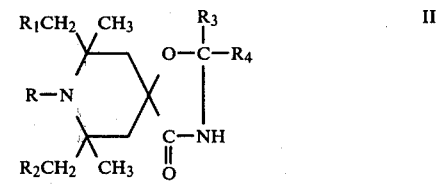

are useful as light stabilizers for polymeric materials, particularly for thermoplastic polymers and automotive finishes. Preferred compounds are those in which R, $R_1$ and $R_2$ are all hydrogen and $R_3$ and $R_4$ together with the carbon atom to which they are attached form a cyclododecylidene ring.

14 Claims, No Drawings

1-OXA-3,8-DIAZASPIRO[4.5]DECANES

This invention relates to 1-oxa-3,8-diaza-4-oxos-piro[4,5]decanes, useful as light stabilizers for polymeric materials.

The invention provides compounds of formula I

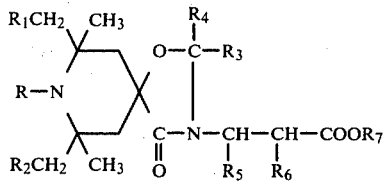

in which

R is hydrogen or $C_{1-8}$alkyl;

$R_1$ and $R_2$, independently, are hydrogen or $C_{1-4}$alkyl;

$R_3$ and $R_4$, independently, are hydrogen, $C_{1-30}$alkyl or benzyl; or $R_3$ is hydrogen or $C_{1-4}$alkyl and $R_4$ is phenyl, ($C_{1-4}$alkyl)phenyl, chlorophenyl, 4-hydroxy-3,5-t.-butyl-phenyl or naphthyl; or $R_3$ and $R_4$ together with the carbon atom to which they are attached form a $C_{5-15}$cycloalkylidene ring which may be unsubstituted or substituted by one $C_{1-4}$alkyl group, or form a group of formula (a)

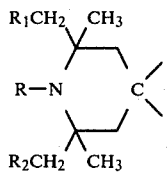

$R_5$ is hydrogen, methyl, phenyl or —COO($C_{1-21}$alkyl);

$R_6$ is hydrogen or methyl; and $R_7$ is hydrogen; a $C_{1-21}$alkyl or $C_{2-21}$alkenyl group which may be unsubstituted or monosubstituted by phenyl or naphthyl and which may be interrupted by oxygen or by a $C_{1-4}$-alkylamine group; phenyl; ($C_{1-12}$alkyl)phenyl; $C_{5-12}$cycloalkyl or an aliphatic hydrocarbon residue having 2–20 carbon atoms which may be interrupted by oxygen or by a $C_{1-4}$alkylimine group and which is substituted by 1–3 groups selected from ($C_{1-21}$alkyl)COO— and groups of formula (b).

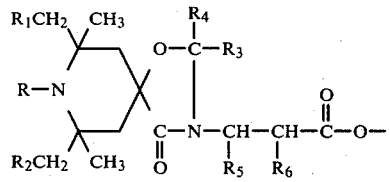

In compounds of formula I, whenever the same symbol appears more than once it may have the same or different significances, unless otherwise stated. All $C_3$ or higher alkyl groups may be either straight chain or branched.

When R is alkyl it is preferably $C_{1-4}$alkyl, more preferably methyl. R is preferably R' where R' is hydrogen or alkyl, more preferably R'' where R'' is hydrogen or methyl, most preferably hydrogen.

$R_1$ and $R_2$, independently, are preferably hydrogen.

$R_3$ is preferably $R_3'$ where $R_3'$ is hydrogen, $C_{1-4}$alkyl or benzyl, or together with $R_4$ and the carbon atom to which they are attached form a $C_{5-12}$cycloalkylidene ring. More preferably $R_3$ is $R_3''$ where $R_3''$ is hydrogen, $C_{1-4}$alkyl or together with $R_4$ and the carbon atom to which they are attached forms a cyclopentylidene, cyclohexylidene or cyclododecylidene ring, preferably cyclododecylidene.

If not taken together with $R_3$, $R_4$ is preferably $R_4'$ where $R_4'$ is $C_{1-12}$alkyl, benzyl or (where $R_3$ is hydrogen or alkyl) phenyl. More preferably $R_4$ is $R_4''$ where $R_4''$ is $C_{1-12}$alkyl. When $R_3$ is hydrogen, then $R_4$ is preferably isopropyl, n-butyl, isobutyl, n-pentyl, isopentyl, hexyl, heptyl, nonyl, undecyl or phenyl, preferably one of the listed alkyl groups. $R_3$ as alkyl is preferably methyl or ethyl. When $R_3$ is methyl, $R_4$ is preferably methyl, ethyl, propyl, hexyl or nonyl. When $R_3$ is ethyl, $R_4$ is preferably ethyl or n-pentyl. $R_3$ and $R_4$ are preferably identical $C_{1-4}$alkyl groups or together with the carbon atom to which they are attached form one of the listed cycloalkylidene rings. Most preferably, $R_3$ and $R_4$ together with the carbon atom to which they are attached form a cyclododecylidene ring.

$R_5$ is preferably $R_5'$ where $R_5'$ is hydrogen or methyl, more preferably hydrogen. $R_6$ is preferably hydrogen.

$R_7$ is preferably $R_7'$ where $R_7'$ is $C_{1-21}$alkyl or $C_{2-22}$alkenyl, either of which may be interrupted by oxygen or a $C_{1-4}$alkylimine group; $C_5$ or $C_6$ cycloalkyl; phenyl($C_{1-4}$alkyl); phenyl; ($C_{1-12}$alkyl)phenyl or a polyvalent saturated group of formula (c) to (m) carrying on any free valency further groups (b) or $C_{1-21}$alkyl carboxylate groups. The groups (c) to (m) are as follows:

$$\text{—(CH}_2\text{)}_{\overline{p}} \quad (c)$$
$$(p = 2-10)$$

$$\begin{array}{c} \text{—CH—CH}_2\text{—} \\ | \\ \text{CH}_3 \end{array} \quad (d)$$

$$\begin{array}{c} \text{—CH—CH}_2\text{—CH}_2\text{—} \\ | \\ \text{CH}_3 \end{array} \quad (e)$$

$$\begin{array}{c} \text{—CH}_2\text{—CH—CH}_2\text{—} \\ | \\ \text{CH}_3 \end{array} \quad (f)$$

$$\text{—CH}_2\text{—CH}_2\text{—O—CH}_2\text{—CH}_2\text{—} \quad (g)$$

$$\begin{array}{c} \text{CH}_3 \\ | \\ \text{—CH}_2\text{—C—CH}_2\text{—} \\ | \\ \text{CH}_3 \end{array} \quad (h)$$

$$\begin{array}{c} \text{CH}_2\text{—CH}_3 \\ | \\ \text{—CH}_2\text{—C—CH}_2\text{—} \\ | \\ \text{CH}_3 \end{array} \quad (i)$$

$$\begin{array}{c} \text{—CH}_2\text{—CH—CH}_2\text{—} \\ | \end{array} \quad (k)$$

$$\begin{array}{c} \text{—CH}_2\text{—CH}_2\text{—N—CH}_2\text{—CH}_2\text{—} \\ | \\ \text{CH}_2\text{—CH}_2\text{—} \end{array} \quad (l)$$

-continued

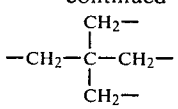 (m)

$R_7$ is more preferably $R_7''$ where $R_7''$ is $C_{1-18}$alkyl or one of the groups (c)–(i).

Preferred compounds are those of formula Ia

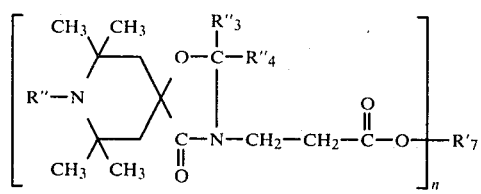 Ia in which n is an integer from 1 to 4, preferably 1 or 2, and more preferred compounds are those of formula Ib

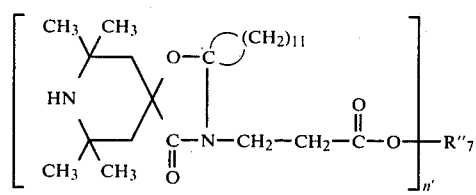 Ib in which n' is 1 or 2.

The compounds of formula I may be prepared by reacting a compound of formula II

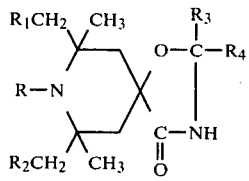 II with a compound of formula III

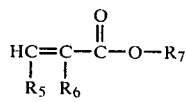 III in the presence of a basic catalyst. When the group $R_7$ contains one or more groups (b), these may be introduced by stepwise reactions before the final reaction of compounds II and III, or, when all groups (b) in the molecule are identical, the compound of formula I may be formed by the reaction of q moles of compound of formula II with a compound of formula IV

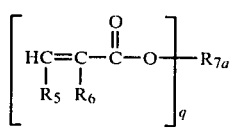 IV where q is an integer from 2 to 4 and $R_{7a}$ is an aliphatic hydrocarbon residue having 2–20 carbon atoms which may be interrupted by oxygen or by a $C_{1-4}$alkylimine group and which bears r groups of formula ($C_{1-21}$alkyl)-COO— where r is 0, 1 or 2 and $(q+r) \leq 4$.

The conditions of the addition reaction are those of the Michael addition, as described in Organic Reactions, Vol. 10 pages 179 ff (1959). Preferably the reaction is carried out in an inert solvent at temperatures of from 50°–150° C., preferably 80°120° C. The alkaline catalyst is preferably an alkali metal, more preferably sodium.

Compounds of formula II and their preparation are described in German published application No. 2 606 026. Compounds of formulae III and IV are known or can be prepared by analogy with known compounds.

Compounds of formula I are useful as stabilizers to protect polymeric materials against degradation by light. Compared with the compounds of formula II, those of formula I have improved solubility and miscibility in solvent systems and in liquid polymers and prepolymers, which makes them useable in a wide range of polymeric materials.

The concentration of compound of formula I employed in the polymeric material is suitably 0.01 to 5% by weight, preferably 0.02 to 1% by weight. The compound may be added before, during or after the polymerization step, and may be added in solid form; in solution, preferably as a liquid concentrate containing from 20–80% by wt. of compound of formula I; or as a solid masterbatch composition containing 20–80% by wt. of compound of formula I and 80–20% by wt. of a solid polymeric material which is identical with or compatible with the polymeric material to be stabilized.

Suitable polymeric materials include plastics materials for example polyethylene, polypropylene, ethylene/propylene copolymers, polyvinyl chloride, polyester; polyamide, polyurethane, polyacrylonitrile, ABS, terpolymers of acrylates, styrene and acrylonitrile, styrene/acrylonitrile and styrene/butadiene. Other plastics materials such as polybutylene, polystyrene, chlorinated polyethylene, polycarbonate, polymethylmethacrylate, polyphenylene oxide, polypropylene oxide, polyacetals, phenol/formaldehyde resins and epoxy resins may also be used. Preferred plastics materials are polypropylene, polyethylene, ethylene/propylene copolymers and ABS. Natural polymers for example natural rubber may also be stabilized, as may lubricating oils containing polymeric material.

The compounds of formula I may be incorporated by known methods into the polymeric material to be stabilized. Of particular importance is blending of the compounds with thermoplastic polymers in the melt, for example in a melt blender or during the formation of shaped articles, including foils, tubes, fibres and foams by extrusion, injection moulding, blow moulding, spinning or wire coating.

It is not essential for the polymeric material to be fully polymerised before mixing with the compounds according to the invention. The compounds may be mixed with monomer, prepolymer or precondensate, and the polymerisation or condensation reaction carried out subsequently. This will of course be the preferred method of incorporation of the compounds into thermosetting polymers, which cannot be melt blended.

The compounds of formula I may be used alone or in combination with other stabilizers, for example antioxidants. Examples include sterically hindered phenols, sulphur or phosphorus-containing compounds or mixtures of these. Examples are benzofuran-2-ones; indolin- 2-ones and sterically hindered phenols such as β-(4-hydroxy-3,5-ditert.-butylphenyl)-propionyl stearate, methane tetrakis-[methylene-3(3',5'-ditert.-butyl-4-hydroxyphenyl-)-propionate], 1,3,3-tris-(2-methyl-4-hydroxy-5-tert.-butylphenyl)-butane, 1,3,5-tris(4-tert.-butyl-3-hydroxy-2,6-dimethylbenzyl)-1,3,5-triazin-2,4,6 (1H, 3H, 5H)-trione, bis (4-tert.-butyl-3-hydroxy-2,6-dimethylbenzyl)dithiolterephthalate, tris (3,5-ditert.-butyl-4-hydroxybenzyl) isocyanurate, the triester of β-(4-hydroxy-3,5-ditert.-butylphenyl) propionic acid with 1,3,5-tris-(2-hydroxyethyl)-5-triazin-2,4,6 (1H, 3H, 5H)-trione, bis [3,3-bis-(4'-hydroxy-3-tert.-butylphenyl)-butyric acid] glycol ester, 1,3,5-trimethyl-2,4,6 tris-(3,5-ditert.-butyl-4-hydroxybenzyl) benzene, 2,2'-methylene-bis-(4-methyl-6-tert.-butylphenyl) terephthalate, 4,4-methylene-bis-(2,6 ditert.-butylphenol), 4,4'-butylidene-bis-(tert.-butylmeta-cresol), 4,4-thio-bis-(2-tert.-butyl-5-methylphenol), 2,2'-methylene-bis-(4-methyl-6-tert.-butylphenol.

Sulphur-containing antioxidative co-stabilizers which may be used include for example distearylthiodipropionate, dilaurylthiodipropionate, methane tetrakis (methylene-3-hexylthiopropionate), methane tetrakis (methylene-3-dodecylthiopropionate) and dioctadecyldisulphide. Phosphorus-containing co-stabilizers include for example trinonylphenyl phosphite, 4,9-distearyl-3,5,8,10-tetraoxadiphosphaspiroundecane, tris-(2,4-ditert.-butylphenyl)phosphite and tetrakis (2,3-ditert.-butylphenyl)-4,4'-biphenylylene diphosphonite. Further additives such as aminoaryl compounds and UV-absorbers and light stabilizers e.g. 2-(2'-hydroxyphenyl)-benzotriazole, 2-hydroxybenzophenone, 1,3-bis-(2'-hydroxybenzoyl)benzene, salicylates, cinnamates, benzoates and substituted benzoates, sterically hindered amines and oxalic acid diamides may be used. Other known types of additives, e.g. flame retardants and antistatic agents, may also be added.

The compounds of formula I are especially suitable for use in organic polymer-containing coatings, particularly automotive finishes.

Automotive finishes are generally solutions or dispersions of organic polymers or polymer precursors in organic solvents. The majority are stoving finishes, which require the application of heat, generally above 100° C., in order to harden the finish in an acceptable time once it has been applied to the primer-coated metal surface. The effect of this heating may be to accelerate the chemical reaction between polymer precursors in a thermosetting system, or to bring about fusion of particles of a thermoplastic polymer.

Many automotive finishes are metallic finishes, which contain flakes of metal, usually aluminium, in order to provide optical effects due to reflection. Such finishes are often two-coat finishes, in which a clear top coat is applied over a base coat containing the pigment and metal flakes. Such two-coat metallic finishes have particular need of UV stabilizers in the top coat, since the polymer in this coat is not protected by light-absorbing pigments, and it is subjected to almost double the normal amount of radiation because of reflection of light from the lower metallic layer.

The compounds of formula I are particularly useful in stoving finishes, particularly in the top coat of two-layer metallic finishes.

The compounds of formula I are suitable for use as UV stabilizers in a wide range of liquid finishes, for example those base on combinations of melamine-formaldehyde resins with oil-modified polyester resins, polyacrylate resins with added crosslinkers, or saturated polyesters; or on self-crosslinked polyacrylate or polyacrylate resin copolymerised with styrene.

Further examples are two-component finishes based on an aliphatic or aromatic di-isocyanate and a hydroxy-group-containing polyacrylate, polyester or polyether resin. Thermoplastic polyacrylate resins may also be used, the latter being particularly useful in metallic finishes, as are also polyacrylate resins with added crosslinkers in combination with melamine-formaldehyde resins etherified with butanol and, further, hydroxy-group-containing polyacrylate resins hardened with aliphatic di-isocyanates.

The compound of formula I may be added to the finish at any stage in its manufacture, and may be added in solid form or in solution, preferably in the form of a liquid concentrate in a hydrocarbon solvent.

The addition of from 0.02-5% by weight, preferably 0.2-2% by weight of one or more compounds of formula I gives a clear improvement in the light- and weather-stability of organic pigments in stoving finishes as well as reducing the tendency to hairline cracking and loss of gloss as the result of weathering. This is surprizingly also found for metallic finishes, and excellent long-term stability of the clear top coat of two-layer metallic finishes is obtained. In such finishes, the compound of formula I may be added to the metallic undercoat, the clear top coar or both, preferably only to the clear top coat.

The following Examples, in which all parts are by weight and all temperatures in degrees Centigrade, illustrate the invention.

EXAMPLE 1

A mixture of 10 parts dimethylsulphoxide, 10 parts 2,2,4,4-tetramethyl-7-oxa-3,20-diazadispiro[5,1,11,2-]heneicosan-21-one and 0.034 parts sodium metal is heated for 2 hours at 120°. Then 9.5 parts methyl acrylate are added over a period of 10 minutes, and the mixture stirred for 5 hours at 110°. The reaction mixture is poured into ice water and extracted with ether, and the ether layer is dried over MgSO₄ and evaporated. The residue is chromatographed on silica gel with a mixture of toluene/dioxane/conc. aqueous ammonia in the ratio 50:50:1 parts by volume, and finally recrystalized from methanol/water.

The product is 2,2,4,4-tetramethyl-7-(β-methoxycarbonyl)ethyl-7-oxa-3,20-diazadispiro[5,1,11,2]heneicosan-21-one of formula

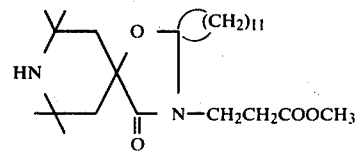

in the form of white crystals, m.p. 109°–112°.

EXAMPLES 2–7

By analogy with Example 1, and using appropriate starting materials, the compounds shown in Table I are obtained.

TABLE I

Compounds of formula

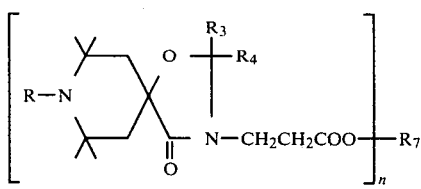

| Example No. | R | $R_3$ | $R_4$ | $R_7$ | n |
|---|---|---|---|---|---|
| 2 | H | $CH_3$ | $CH_3$ | $CH_3$ | 1 |
| 3 | H | $CH_3$ | $CH_3$ | $-CH_2CH(C_4H_9)(C_2H_5)$ | 1 |
| 4 | H | $CH_3$ | $CH_3$ | $-C_{18}H_{37}$ | 1 |
| 5 | $CH_3$ | $-(CH_2)_{11}-$ | | $-CH_3$ | 1 |
| 6 | $CH_3$ | $-(CH_2)_{11}-$ | | $-CH_2CH(C_4H_9)(C_4H_5)$ | 1 |
| 7 | H | $-(CH_2)_{11}-$ | | $-CH_2CH_2-$ | 2 |

Application Example (A)

0.5% by wt. of the compound of Example 1 is worked into polypropylene (containing no UV stabilizer) in a kneading mixer at 180°. The resulting mass is pressed into a 3 mm thick plate, and also into a 0.3 mm thick film. The film is illuminated in an Atlas Weatherometer WRC 600 with a xenon lamp, and the damage caused by UV light is measured by the growth in intensity of the IR carboxyl band absorption at 5.8μ. According to test method DIN 53453, the change in impact strength of samples cut from the 3 mm plate is measured after exposure in the Atlas Weatherometer. In both cases the results obtained are better than those using unstabilized polymer.

Application Example (B)

A two-layer metallic finish is prepared having the following composition:

(a) base coat 12.6 parts commercial polyacrylate resin, with added cross-linking as defined in DIN 53 186 (Viacryl SC 344, Vianova, Vienna, supplied as 50% solution in xylene/butanol 4:1)

2.19 parts commercial butanol-etherified melamine resin, medium reactive, prepared by condensation of 1 mol melamine with 3–6 moles formaldehyde, etherified with 3–6 mole butanol according to DIN 53 187 (Maprenal MF 800, Casella, supplied as 72% solution is isobutanol)

0.96 parts butanol
0.26 parts colloidal silicic acid
7.05 parts xylene
52.0 parts of a 20% cellulose acetate butyrate solution of the following composition by weight:
  20% cellulose acetate butyrate: acetyl content 13.6%, butyryl content 38.7%, hydroxyl content 1.25%, viscosity of 20% solution in acetone = 200 cp
  10% butanol
  35% xylene
  35% butyl acetate
6.80 parts non-leafing aluminium paste, supplied as 65% suspension in alkylglycol acetate according to DIN 55 923
18.14 parts butyl acetate
0.3 parts copper phthalocyanine blue (C.I. Pigment Blue 15:1)

(b) top coat 80.00 parts polyacrylate resin (as in the base coat)
13.75 parts melamine resin (as in the base coat)
4.50 parts butyl glycollate
7.50 parts aromatic hydrocarbon solvent, b.p. 186°–212°
6.00 parts aromatic hydrocarbon solvent, b.p. 155°–178°

(c) application

The base coat is applied to primer-coated metal plates by spraying, giving a layer approx. 20 μm thick, without UV stabilizer. After drying of the base coat, the plates are sprayed with (i) top coat as in (b) above, without UV stabilizer or
(ii) top coat as in (b) above, containing 1 part (i.e. 1% by wt.) of the compound of Example 1b, added as an 80% solution is xylene, and stoved at 140° for 30 minutes. Exposure tests show superior results for the plates coated with topcoat (ii).

The compounds of Examples 2–7 can be used in analogous manner to Application Examples A and B.

What is claimed is:

1. A compound of formula I

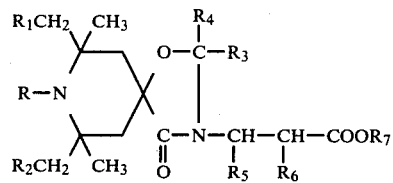

in which

R is hydrogen or $C_{1-8}$alkyl;

$R_1$ and $R_2$, independently, are hydrogen or $C_{1-4}$alkyl;

$R_3$ and $R_4$, independently, are hydrogen, $C_{1-30}$alkyl or benzyl; or $R_3$ is hydrogen or $C_{1-4}$alkyl and $R_4$ is phenyl, ($C_{1-4}$alkyl)phenyl, chlorophenyl, 4-hydroxy-3,5-t.-butyl-phenyl or naphthyl; or $R_3$ and $R_4$ together with the carbon atom to which they are attached form a $C_{5-15}$cycloalkylidene ring which may be unsubstituted or substituted by one $C_{1-4}$alkyl group, or form a group of formula (a)

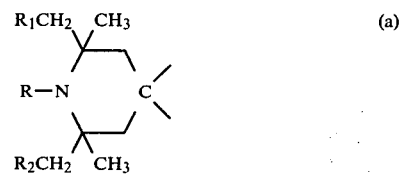

$R_5$ is hydrogen, methyl, phenyl or $-COO(C_{1-21}$alkyl);

$R_6$ is hydrogen or methyl; and $R_7$ is hydrogen; a $C_{1-21}$alkyl or $C_{2-21}$alkenyl group which may be unsubstituted or monosubstituted by phenyl or naphthyl and which may be interrupted by oxygen or by a $C_{1-4}$-alkylimine group; phenyl; ($C_{1-12}$alkyl)phenyl; $C_{5-12}$cycloalkyl or an saturated aliphatic hydrocarbon residue having 2-20 carbon atoms which may be interrupted by oxygen or by a $C_{1-4}$alkylimine group and which is substituted by 1-3 groups selected from $(C_{1-21}\text{alkyl})COO-$ and groups of formula (b).

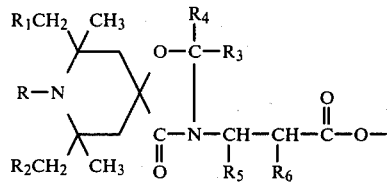
(b)

2. A compound according to claim 1 of formula Ia

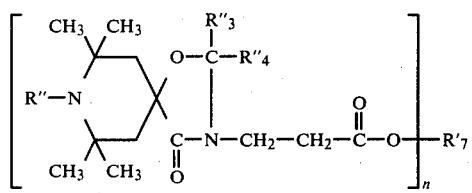
Ia in which
n is an integer from 1 to 4,
R'' is hydrogen or methyl,
$R_3''$ is hydrogen or $C_{1-4}$alkyl,
$R_4''$ is $C_{1-12}$alkyl or $R_3''$ and $R_4''$ together with the carbon atom to which they are attached form a cyclopentylidene, cyclohexylidene or cyclododecylidene ring and
$R_7'$ is $C_{1-21}$alkyl or $C_{2-22}$alkenyl, either of which may be interrupted by oxygen or a $C_{1-4}$alkylamine group; $C_5$ or $C_6$ cycloalkyl; phenyl($C_{1-4}$alkyl); phenyl; ($C_{1-12}$alkyl) phenyl or a polyvalent saturated group of formula (c) to (m)

 (c)
(p = 2-10)

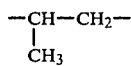 (d)

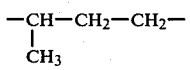 (e)

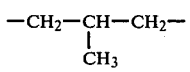 (f)

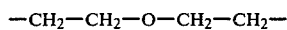 (g)

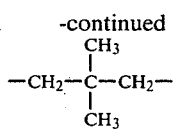 (h)

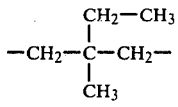 (i)

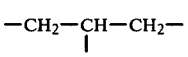 (k)

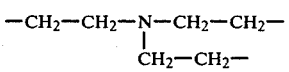 (l)

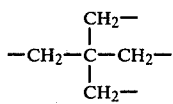 (m)

carrying on any free valency further groups (b), defined in claim 1, or $C_{1-21}$alkyl carboxylate groups.

3. A compound according to claim 2 of formula Ib

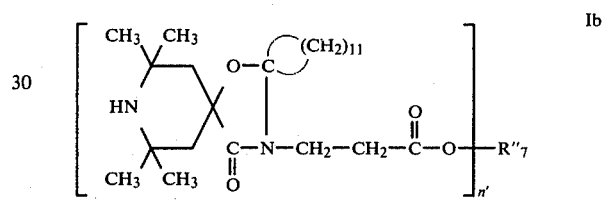
Ib in which
n' is 1 or 2, and
$R_7''$ is $C_{1-18}$alkyl or one of the groups (c)-(i), stated in claim 2.

4. A compound of claim 1 in which R is a hydrogen.
5. A compound of claim 1 in which R is $C_{1-4}$alkyl.
6. A compound of claim 1 in which R is methyl.
7. A compound of claim 1 in which $R_1$ and $R_2$ are, independently, hydrogen.
8. A compound of claim 1 in which $R_3$ and $R_4$ are identical $C_{1-4}$alkyl groups or taken together with the carbon atom to which they are attached a cycloalkylidene ring.
9. A compound of claim 1 where $R_3$ taken together with $R_4$ and the carbon atom to which they are attached form a $C_{5-12}$cycloalkylidene ring.
10. A compound of claim 1 in which $R_3$ together with $R_4$ and the carbon atom to which they are attached form a cyclododecylidene ring.
11. A compound of claim 1 in which $R_5$ is hydrogen.
12. A compound of claim 1 in which $R_6$ is hydrogen.
13. A compound of claim 2 in which n is 1 or 2.
14. The compound of claim 1 which is 2,2,4,4-tetramethyl-7-($\beta$-methoxycarbonyl)ethyl-7-oxa-3,20-diazadispiro [5,1,11,2]heneicosan-21-one.

* * * * *